US010451168B2

(12) United States Patent
Ture et al.

(10) Patent No.: US 10,451,168 B2
(45) Date of Patent: Oct. 22, 2019

(54) FLUID CONDITION MONITORING DEVICE

(71) Applicant: Sikorsky Aircraft Corporation, Stratford, CT (US)

(72) Inventors: Cody Michael Ture, Fairport, NY (US); David Ortiz, Rochester, NY (US); Carl S. Byington, Pittsford, NY (US); Carl Palmer, Pittsford, NY (US); John R. Farnach, Henrietta, NY (US); Ryan Brewer, Rochester, NY (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 108 days.

(21) Appl. No.: 15/555,203

(22) PCT Filed: Jan. 5, 2016

(86) PCT No.: PCT/US2016/012158
§ 371 (c)(1),
(2) Date: Sep. 1, 2017

(87) PCT Pub. No.: WO2016/140731
PCT Pub. Date: Sep. 9, 2016

(65) Prior Publication Data
US 2018/0051793 A1    Feb. 22, 2018

Related U.S. Application Data

(60) Provisional application No. 62/128,551, filed on Mar. 5, 2015.

(51) Int. Cl.
*F16H 57/04*    (2010.01)
*B64D 45/00*    (2006.01)
(Continued)

(52) U.S. Cl.
CPC ......... *F16H 57/0405* (2013.01); *B64D 45/00* (2013.01); *F01M 11/10* (2013.01);
(Continued)

(58) Field of Classification Search
CPC .... F16H 57/0405; G01N 27/06; G01N 33/30; B64D 45/00; B64D 35/00;
(Continued)

(56) References Cited

U.S. PATENT DOCUMENTS 4,635,473 A * 1/1987 Hochstein .......... G01N 33/2888
73/114.55
5,540,086 A 7/1996 Park et al.
(Continued)

OTHER PUBLICATIONS

Notification of Transmittal of the International Search Report for International Application No. PCT/US2016/012158 dated May 10, 2016; dated Jun. 9, 2016; 9 pages.
(Continued)

*Primary Examiner* — Daniel S Larkin
*Assistant Examiner* — Anthony W Megna Fuentes
(74) *Attorney, Agent, or Firm* — Cantor Colburn LLP

(57) ABSTRACT

A fluid condition monitoring device includes a sensing assembly including a sensor and a transducer, the sensor to sense a property of the fluid and the transducer to apply a test signal to the fluid and receive a return signal from the fluid; a control assembly coupled to the sensing assembly, the control assembly including a controller and an input/output interface, the controller interfacing with the transducer to generate fluid condition information in response to the return signal; and an interface assembly coupled to the control assembly, the interface assembly including a connection to the input/output interface to transmit the fluid condition information to an external system.

13 Claims, 6 Drawing Sheets

(51) Int. Cl.
  *G01N 27/06* (2006.01)
  *G01N 33/30* (2006.01)
  *F16N 29/00* (2006.01)
  *F01M 11/10* (2006.01)
  *B64D 35/00* (2006.01)

(52) U.S. Cl.
  CPC ............ *F16N 29/00* (2013.01); *G01N 27/06* (2013.01); *G01N 33/30* (2013.01); *B64D 35/00* (2013.01); *B64D 2045/0085* (2013.01); *F16N 2200/02* (2013.01); *F16N 2200/12* (2013.01); *F16N 2200/20* (2013.01); *F16N 2210/08* (2013.01); *F16N 2210/12* (2013.01)

(58) Field of Classification Search
  CPC ............ B64D 2045/0085; F16N 29/00; F16N 2210/12; F16N 2200/02; F16N 2200/12; F16N 2200/20; F16N 2210/08; F01M 11/10
  See application file for complete search history.

(56) References Cited

U.S. PATENT DOCUMENTS

| | | | |
|---|---|---|---|
| 5,581,648 A | 12/1996 | Sahagen | |
| 5,929,754 A * | 7/1999 | Park | G01N 33/2888 324/663 |
| 6,433,560 B1 | 8/2002 | Hansen et al. | |
| 6,822,461 B2 * | 11/2004 | Klun | G01N 27/226 324/698 |
| 7,043,402 B2 | 5/2006 | Phillips et al. | |
| 7,239,155 B2 | 7/2007 | Byington et al. | |
| 7,504,835 B2 | 3/2009 | Byington et al. | |
| 2003/0101801 A1 | 6/2003 | Wilson et al. | |
| 2003/0222656 A1 | 12/2003 | Phillips et al. | |
| 2005/0145019 A1 | 7/2005 | Matsiev et al. | |
| 2006/0229776 A1 * | 10/2006 | Lvovich | G01N 33/2835 324/698 |
| 2013/0250303 A1 * | 9/2013 | Shirata | B25J 9/102 356/436 |
| 2014/0260678 A1 * | 9/2014 | Jentoft | G01L 5/16 73/862.046 |

OTHER PUBLICATIONS

Written Opinion of the international Searching Authority for International Application No. PCT/US2016/012158 dated May 10, 2016; dated Jun. 9, 2016; 5 pages.

* cited by examiner

FLUID CONDITION MONITORING DEVICE

CROSS REFERENCE TO RELATED APPLICATIONS

This application is a National Stage application of PCT/US2016/012158, filed Jan. 5, 2016, which claims the benefit of U.S. Provisional Patent Application No. 62/128,551, filed Mar. 5, 2015, both of which are incorporated by reference in their entirety herein.

STATEMENT REGARDING FEDERALLY SPONSORED RESEARCH OR DEVELOPMENT

This invention was made with Government support with the United States Navy under Contract No. N68335-08-C-0025. The government therefore has certain rights in this invention.

BACKGROUND

The subject matter disclosed herein relates generally to the field of fluid analysis and, more particularly, to a fluid condition monitoring device contained in a robust mechanical package.

DESCRIPTION OF RELATED ART

Aircraft mechanical components require wear protection fluids such as drive train lubricants and engine oils to keep the aircraft components operating in an efficient manner. Lubricating fluids can become degraded or contaminated by internal or external sources or accumulate component wear debris due to pitting, spalling, corrosion-induced fatigue, or other mechanisms. Further, water infiltration or chemical changes can degrade the lubricant and can affect oil-wetted component lifetimes and maintenance requirements.

Offline lubricant monitoring of oil-wetted mechanical components is being widely used for diagnostic and prognostic assessment of the health of these mechanical components. In-situ lubricant monitoring devices need to operate in harsh environments, especially in aircraft, rotorcraft, and industrial applications. Lubricant monitoring devices need to withstand mechanical forces, such as vibration and shock, and environmental conditions, such as high pressure and high temperature.

BRIEF SUMMARY

According to an aspect of the invention, a lubricant condition monitoring device includes a fluid condition monitoring device including a sensing assembly including a sensor and a transducer, the sensor to sense a property of the fluid and the transducer to apply a test signal to the fluid and receive a return signal from the fluid; a control assembly coupled to the sensing assembly, the control assembly including a controller and an input/output interface, the controller interfacing with the transducer to generate fluid condition information in response to the return signal; and an interface assembly coupled to the control assembly, the interface assembly including a connection to the input/output interface to transmit the fluid condition information to an external system.

In addition to one or more of the features described above or below, or as an alternative, further embodiments could include wherein the sensor measures one or both of relative humidity and temperature of the fluid.

In addition to one or more of the features described above or below, or as an alternative, further embodiments could include a potting material encompassing the sensor.

In addition to one or more of the features described above or below, or as an alternative, further embodiments could include wherein the transducer includes a first electrode and a second electrode.

In addition to one or more of the features described above or below, or as an alternative, further embodiments could include an insulator positioned between the electrode and a second electrode.

In addition to one or more of the features described above or below, or as an alternative, further embodiments could include wherein the sensing assembly includes a biasing member to secure the transducer and the sensor in position.

In addition to one or more of the features described above or below, or as an alternative, further embodiments could include wherein the controller performs a self-calibration process.

In addition to one or more of the features described above or below, or as an alternative, further embodiments could include wherein the self-calibration process includes automatic gain selection to adjust a gain across a plurality of test signal frequencies.

In addition to one or more of the features described above or below, or as an alternative, further embodiments could include wherein the self-calibration process includes automatic test signal selection to select a subset of test frequencies for use in generating the fluid condition information.

In addition to one or more of the features described above or below, or as an alternative, further embodiments could include wherein the sensing assembly includes a first circuit board, the control assembly includes a control circuit board, and further comprising a flexible circuit board interconnecting the first circuit board and the control circuit board.

In addition to one or more of the features described above or below, or as an alternative, further embodiments could include wherein the control assembly includes a control circuit board mounted in a board support, the board support including at least one shock absorber to absorb force at the control assembly.

In addition to one or more of the features described above or below, or as an alternative, further embodiments could include wherein the fluid condition monitor is configured to determine at least one of water content, incorrect fluid addition, lubricant oxidation degradation, additive depletion, or viscosity.

In addition to one or more of the features described above or below, or as an alternative, further embodiments could include wherein the fluid condition information comprises at least one of dielectric properties, conductivity, and fluid impedance.

In addition to one or more of the features described above or below, or as an alternative, further embodiments could include wherein the fluid condition monitoring device is positioned in at least one of an in-line flow path, an on-line flow path and an off-line flow path.

In addition to one or more of the features described above or below, or as an alternative, further embodiments could include wherein the fluid is a lubricant Other aspects, features and techniques of the invention will become more apparent from the following description taken in conjunction with the drawings.

BRIEF DESCRIPTION OF THE SEVERAL VIEWS OF THE DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which like elements are numbered alike in the several FIGURES:

DETAILED DESCRIPTION

Exemplary embodiments are described with reference to a lubricant condition monitoring device for use with a gearbox of a mobility platform or fixed asset. It is understood that embodiments may more generally apply to a fluid condition monitoring device for use with a variety of systems, such as hydraulic systems, coolant systems, etc. Therefore, although embodiments are described with reference to a lubricant condition monitoring device, it is understood that embodiments of the invention are not intended to be limited to the analysis of lubricants, but may apply to a variety of fluids.

Figure 1:
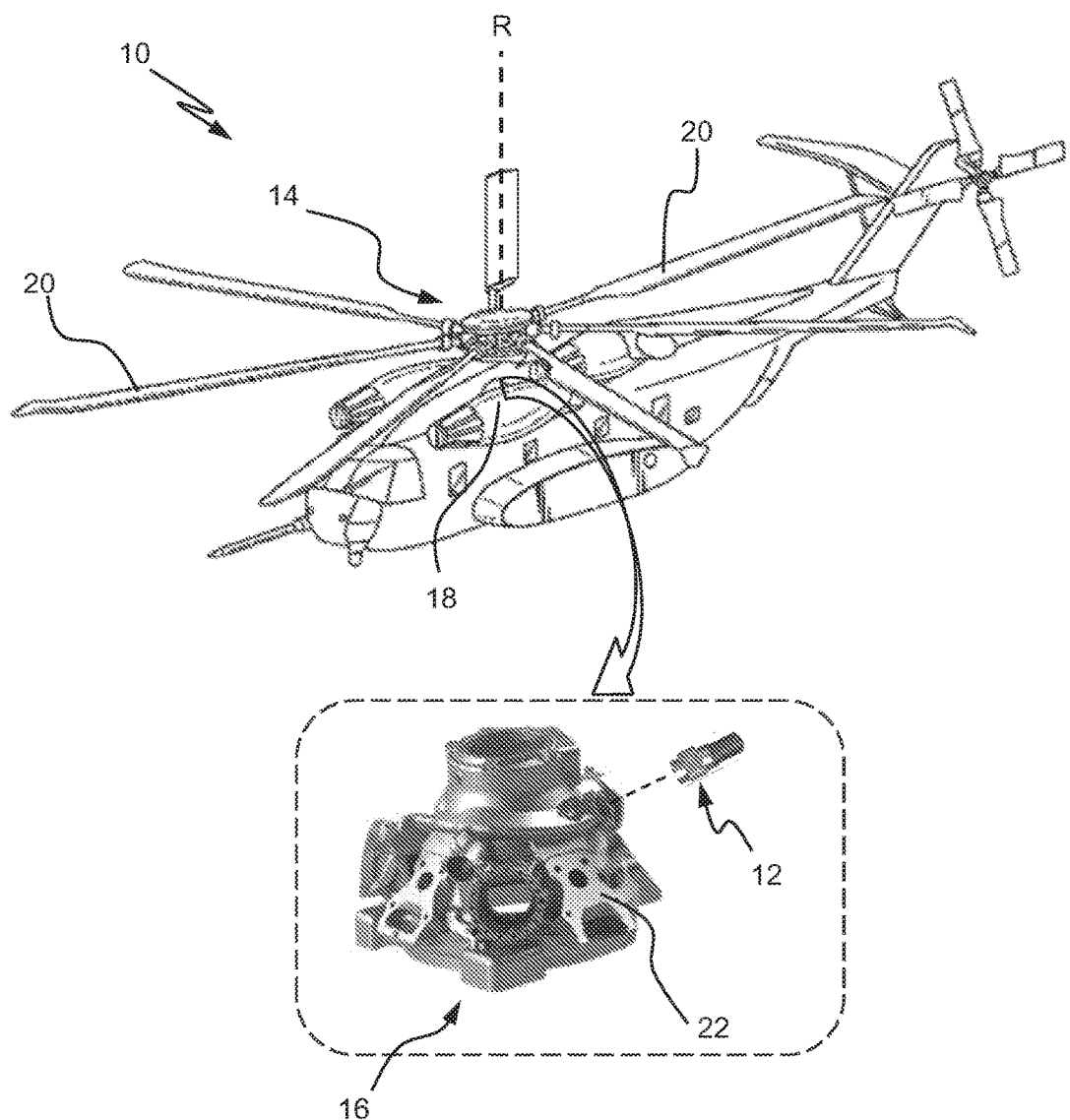
FIG. 1 depicts a vehicle and a gear box in an exemplary embodiment.

FIG. 1 illustrates an exemplary rotary wing aircraft 10 having a gearbox 16 with a lubricant condition monitoring device 12 that provides lubrication condition information. Lubricant may include oils or other lubricating fluids. Although embodiments are described with reference to lubricant monitoring, the lubricant condition monitoring device 12 may be used with other fluids (e.g., coolants, transmission fluids, etc.) and may be more generally referred to as a fluid condition monitoring device.

Exemplary aircraft 10 includes a main rotor assembly 14 that is driven about an axis of rotation R by one or more engines 18. The main rotor assembly includes a multiple of rotor blades 20 mounted to rotor assembly 14 that are driven for rotation about axis R through a main gearbox 16. Lubricant condition monitoring device 12 may provide lubricant condition monitoring via a single, ruggedized, device. Lubricant condition monitoring device 12 can be positioned in-line with lubricant flow through main gearbox 16 and can be selectively coupled to housing 22 of main gearbox 16. In other embodiments, the lubricant condition monitoring device 12 may be mounted in a flow through device, separate from the housing 22. More generally, the lubricant condition monitoring device 12 may be located anywhere there is flowing lubricant (or fluid), including oil coolers and associated. As a result, lubricant condition monitoring device 12 provides in-line, real-time monitoring of lubricant as it travels from main gearbox 16. The lubricant condition monitoring device 12 may also be utilized in an on-line or offline configuration, as described in further detail herein.

Figure 2:
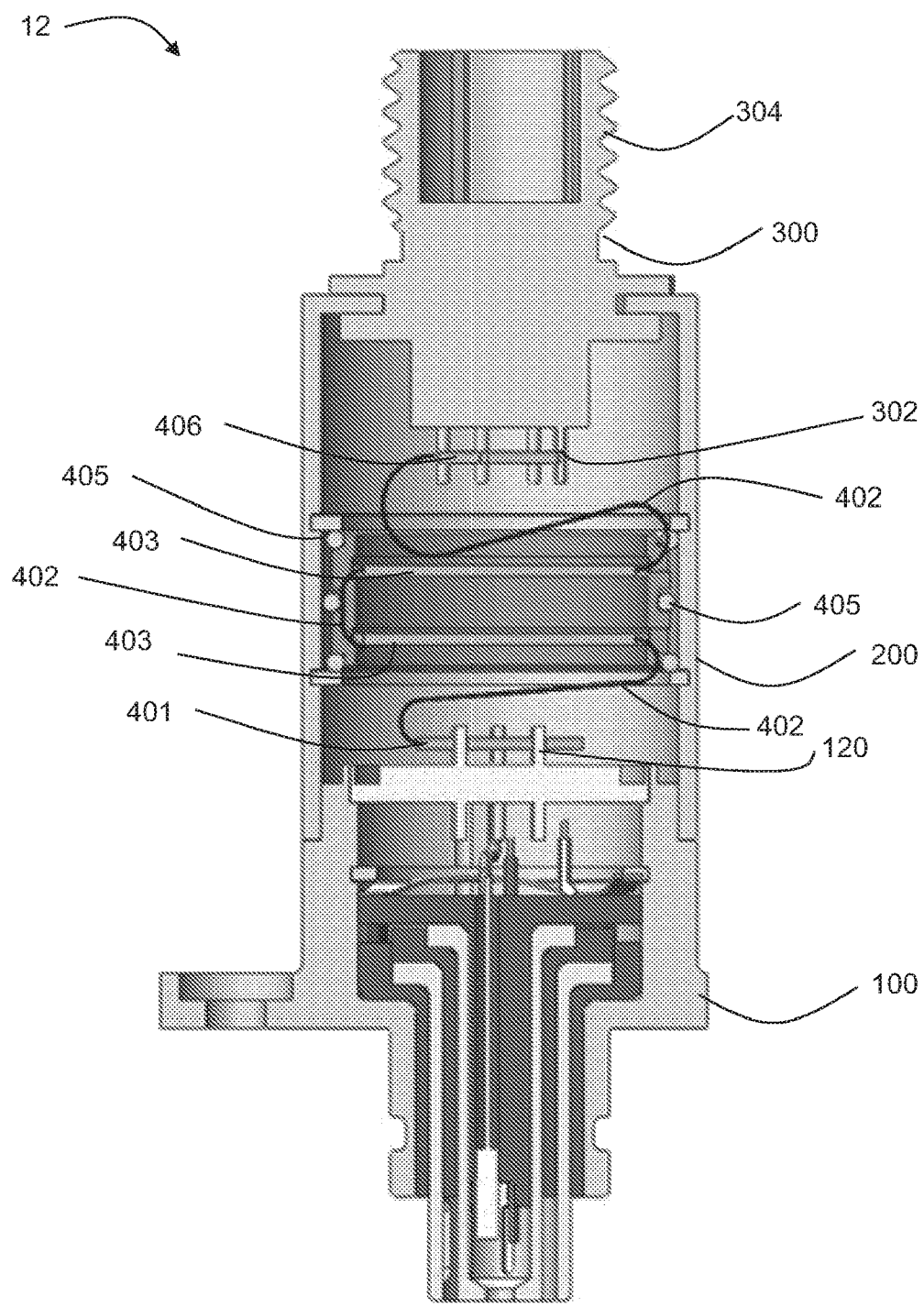
FIG. 2 is a cross-sectional view of lubricant condition monitoring device in an exemplary embodiment.

FIG. 2 is a cross-sectional view of the lubricant condition monitoring device 12 in an exemplary embodiment. The lubricant condition monitoring device 12 includes a sensing assembly 100, a control assembly 200 and an interface assembly 300. The sensing assembly 100 senses one or more parameters of the lubricant. The control assembly 200 includes components to receive outputs from sensors in the sensing assembly 100, generate test signals and process return signals from a transducer in the sensing assembly 100 and provide an output to the interface assembly 300. Control assembly 200 may detect lubricant condition information such as water content, incorrect fluid addition, lubricant oxidation degradation, additive depletion, viscosity, or the like. Interface assembly 300 provides a connection point for power and a communications interface to an external system.

Figure 3:
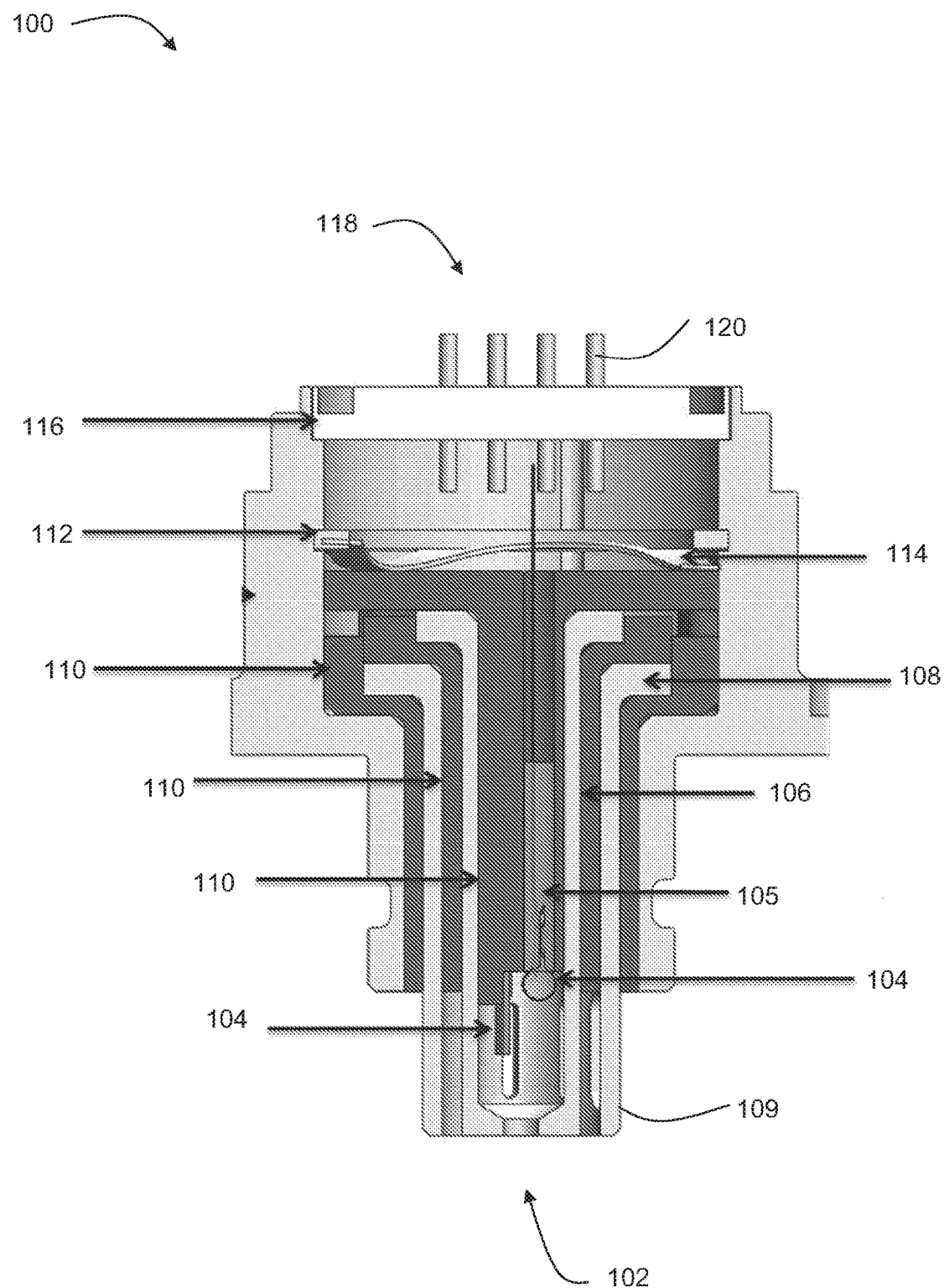
FIG. 3 is a cross-sectional view of a sensing assembly in an exemplary embodiment.

FIG. 3 is a cross-sectional view of sensing assembly 100 in an exemplary embodiment. The sensing assembly 100 includes a first end 102 that is placed in contact with the lubricant. First end 102 may contain one or more sensors 104, to measure properties of the lubricant. Sensors 104 may be encased in a potting compound 105. In an exemplary embodiment, sensors 104 include a relative humidity sensor and a temperature sensor. The sensing assembly 100 also includes a transducer 109 having a first electrode 106 and a second electrode 108. The first electrode 106 and a second electrode 108 may be arranged concentrically, such that the first electrode 106 is positioned within the second electrode 108. The first electrode 106 and the second electrode 108 extend to define the first end 102. A series of insulators 110 electrically isolate the first electrode 106 and the second electrode 108 from each other and other components.

A snap ring 112 provides a shoulder internal to the sensing assembly 100. A biasing member 114 (e.g., a wave spring) is positioned between the snap ring 112 and one of the insulators 110. The biasing member 114 applies a force to the insulators 110, first electrode 106 and second electrode 108 to hold these components in a secure, ruggedized manner. A feed through plate 116 is secured at a second end 118 of the sensor assembly 100. The feed through plate 116 includes conductive pins 120 extending therethrough. The feed through plate 116 may be a ceramic plate that is welded or otherwise sealed to the housing of the sensing assembly 100. The conductive pins 120 provide a connection point between the components of the sensing assembly 100 and the control assembly 200.

Figure 4:
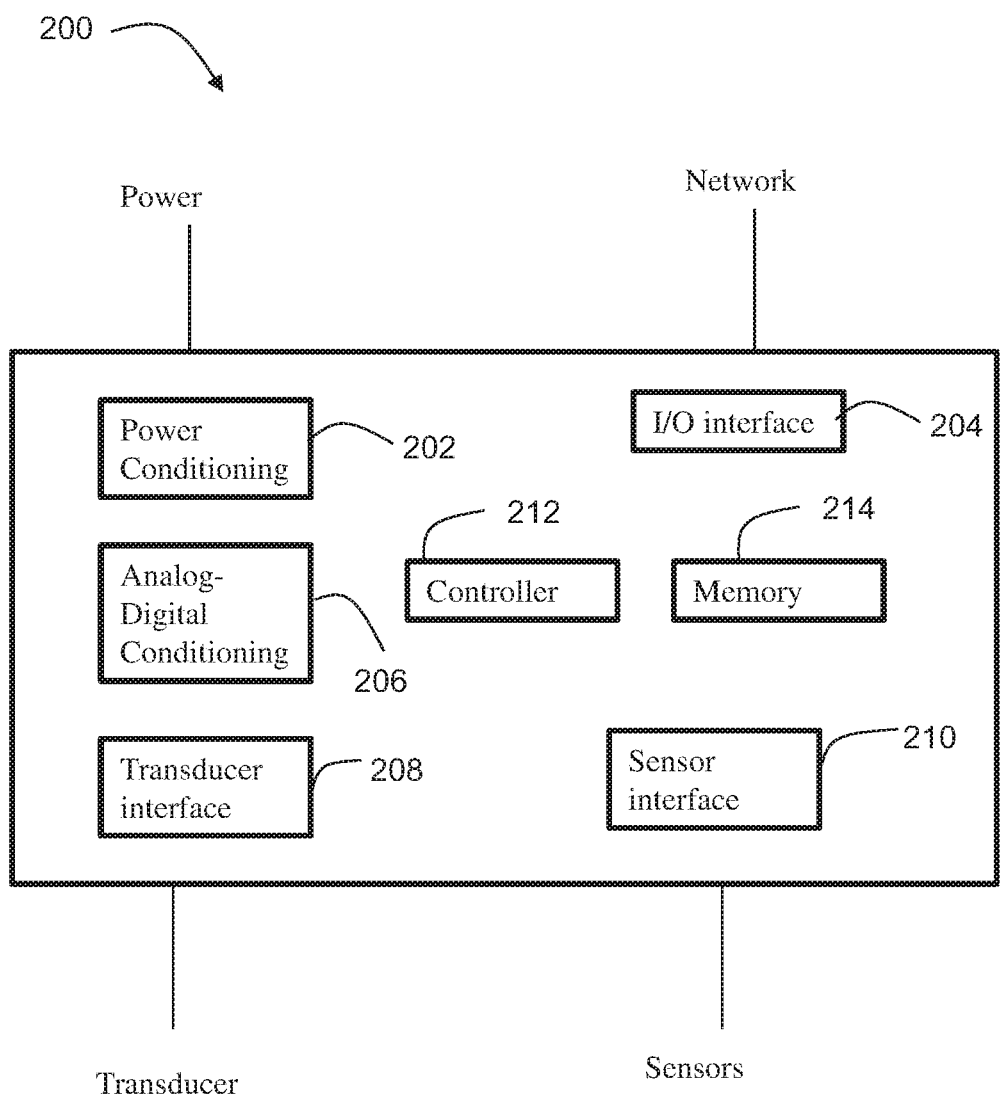
FIG. 4 depicts components of a control assembly in an exemplary embodiment.

FIG. 4 depicts components of the control assembly 200 in an exemplary embodiment. The control assembly 200 receives power from interface assembly 300, and includes a power conditioning unit 202 for modifying the received power (e.g., AC-DC conversion, filtering, step-up, step-down, etc.). An input-output interface 204 communicates with a network to receive commands and provide output data, including lubricant condition information, to the network. The input-output interface 204 may be a serial interface (e.g., RS422, RS232, RS485, etc.). An analog and digital signal conditioning unit 206 provides for manipulating both analog and digital signals, and performing analog-to-digital conversions. The analog and digital signal conditioning unit 206 may process signals from the sensors 104 and the transducer 109. A transducer interface 208 provides a test signal to the first electrode 106 and receives a return signal received on the second electrode 108. The test signal may be in the form of a broadband signal, sine wave, or beat pulse, etc. A sensor interface 210 receives signals from the sensors 104.

A controller 212 controls operation of the lubricant condition monitoring device 12. Controller 212 may be implemented as a microcontroller, DSP, microprocessor or similar device and includes a memory 214. Memory 214 may store reference data (e.g., look up tables) that may include impedance values for a lubricant at different frequencies of a test signal.

In operation, control assembly 200 uses transducer 109 to measure the electrochemical response of the lubricant and estimates the lubricant health through a lubricity impedance model. The system electrochemically models the lubricant as a modified Randles circuit to assess changes in the dielectric properties and conductivity and fluid impedance of the lubricant as it degrades by aging (due to additive depletion, varnish accumulation, oxidation, or the like) or the presence of contaminants such as water or an incorrect lubricant. The transducer 109 injects a multi-frequency AC voltage test signal into the lubricant and measures the response at the frequency of the test signal. The impedance of the lubricant can then be determined by comparing the differences between the test signal and the return signal. The control assembly 200 generates lubricant condition information, which may include dielectric properties, conductivity, and impedance.

Controller 212 may execute calibration processes, including automatic gain selection and automatic test signal selection. Automatic gain selection may be performed by setting the transducer interface 208 to loop back the test signal as the return signal. In other words, the test signal serves as the return signal, without being injected in the lubricant. Controller 212 generates the test signal across a plurality of frequencies and evaluates the amplitude of the return signal across the frequencies. If the amplitude of the return signal is low or high, then the gain of the transducer interface 208 may be increased or decreased accordingly, at multiple frequencies. The purpose of the automatic gain selection is to ensure that the test signal is within a valid range of voltage values. During normal operation, the controller 212 will examine the maximum and minimum values of the return signal to ensure a minimum dynamic range is being achieved. User defined thresholds are stored in memory and used to define the acceptable dynamic range. If this range is not met, the controller 212 will utilize the automatic gain selection to assign new gain values for each sub-range of frequencies, in order to achieve an optimal dynamic range, and repeat the signal interrogation.

Controller 212 may also perform automatic test signal selection to determine which frequencies should be used by the transducer 109 to test the lubricant. Controller 212 works in conjunction with transducer interface 208 to generate test signals across numerous frequencies (e.g., 1000 frequencies). The controller 212 receives the return signals from transducer 109 across all the test frequencies. The return signals from transducer 109 are used to generate impedance values at each frequency. The frequencies and impedance values are then compared to reference signals in memory 214 (e.g., a look up table) to identify a subset of frequencies (e.g., about 10-20 frequencies) that are to be used to test the lubricant.

Referring to FIG. 2, the interface assembly 300 is secured to the control assembly 200, opposite the sensing assembly 100. The interface assembly 300 includes a plurality of conductive pins 302. Pins 302 may provide power and the network interface to control assembly 200. An exposed end of interface assembly 300 includes a threaded connector 304 for receiving a cable. The results of the lubricant condition monitoring by control assembly 200 may be transmitted to external systems, such as a pilot indicator or a health and monitoring system.

FIG. 2 also depicts electrical interconnection between the sensing assembly 100, control assembly 200 and interface assembly 300. A first connector board 401 interfaces with conductive pins 120. A flexible circuit board 402 provides electrical connections between the first connector board 401 and a control circuit board 403. If the control assembly 200 includes multiple circuit boards, then each control circuit board 403 may be coupled by a flexible circuit board 402. A second connector board 406 interfaces with conductive pins 302. A flexible circuit board 402 provides electrical connections between the second connector board 406 and a control circuit board 403. The use of rigid circuit boards 401, 403 and 406, joined by flexible circuit boards 402 allows the lubricant condition monitoring device 12 to have a compact size.

Figure 5:
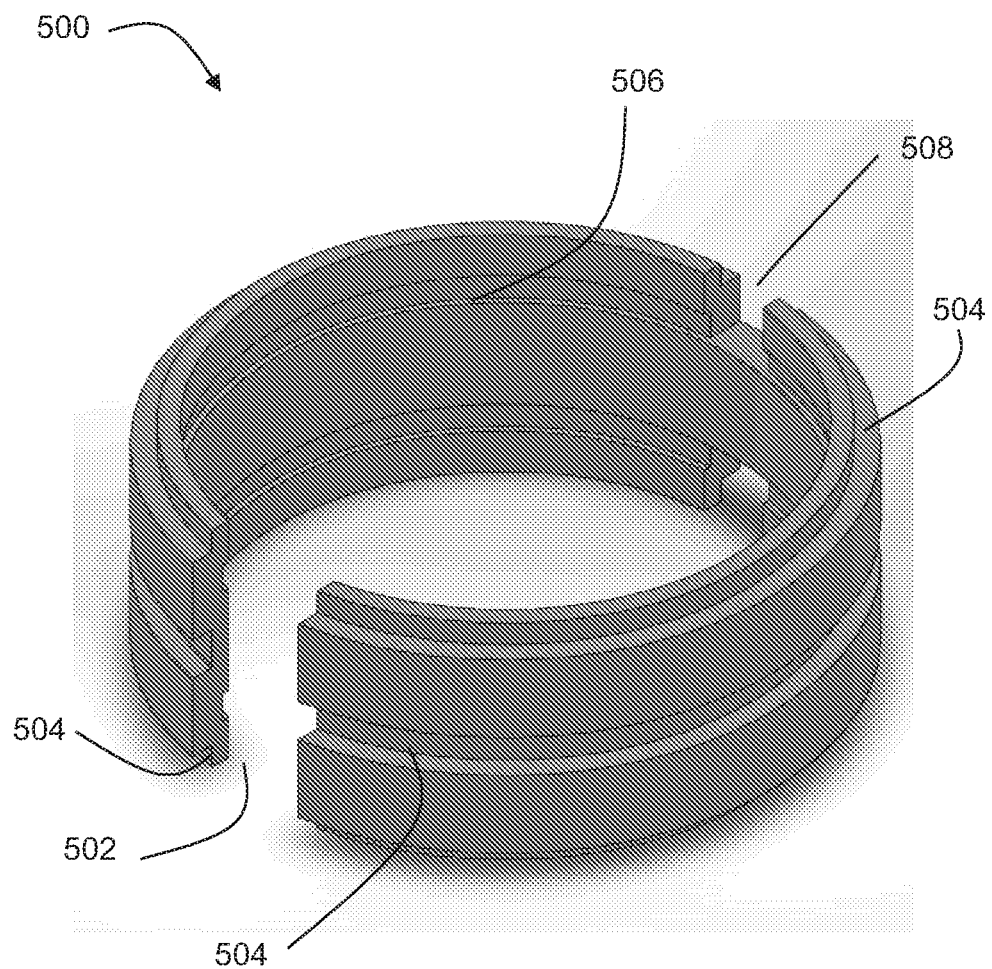
FIG. 5 is a perspective view of a board support in an exemplary embodiment.

FIG. 5 depicts a board support 500 that is used to secure control circuit boards. 403 in the control assembly 200. Board support 500 is a generally cylindrical member having an opening 502 in the cylinder wall. Opening 502 allows the board support 500 to flex and serve as a shock absorber to absorb force at the control assembly 200. Opening 502 also provides in ingress point for potting compound to encase components inside the board support 500. The outer surface of board support 500 includes at least one groove 504 that receives an o-ring 405 (FIG. 2). The o-rings 405 serve as a shock absorber to absorb force at the control assembly 200. The inner wall of the board support 500 includes interior groove(s) 506 to support control circuit board(s) 403. The wall of board support 500 may include one or more notches 508 to further allow the board support 500 to flex and serve as a shock absorber to absorb force. The flexure of the board support and the use of o-rings 405 help to prevent force from being transmitted to control circuit board(s) 403.

Figure 6:
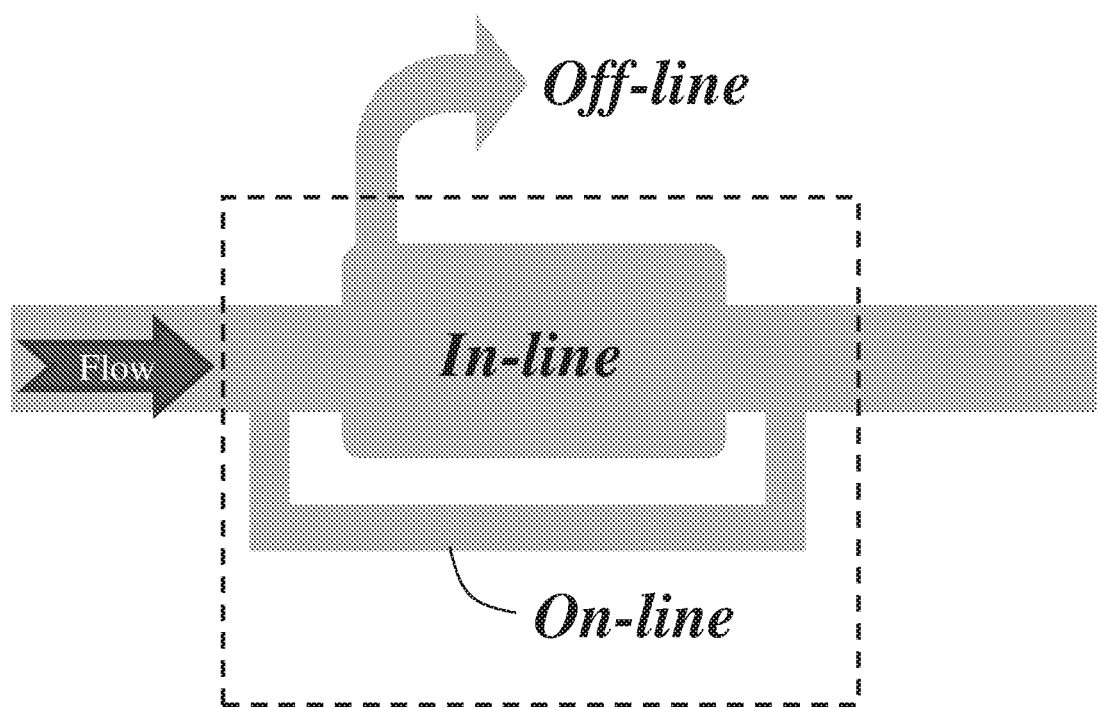
FIG. 6 illustrates various arrangements for use of the lubricant condition monitoring device.

FIG. 6 depicts exemplary lubricant condition assessment topologies that may be employed with the lubricant condition monitoring device 12. In one topology, referred to as an in-line flow path, lubricant from the gearbox passes through the lubricant condition monitoring device 12 for evaluation. In an alternate topology, referred to as an on-line flow path, a portion of the lubricant is diverted from the full flow path, passes through the lubricant condition monitoring device 12, and then returns to the full flow path. This on-line flow path topology may include additional filtering of the lubricant. In an alternate topology, referred to as an off-line flow path, lubricant is removed from the system and passes through the lubricant condition monitoring device 12 for analysis, for example at a test station. The off-line flow path may also be part of a "kidney loop" which provides additional filtering of the lubricant prior to returning clean or otherwise revitalized oil.

Embodiments provide a multi-element sensing assembly 100, collocated with supporting electronics in controller assembly 200, in a robust mechanical package. Embodiments include a high pressure and high temperature sealing interface for use in harsh fluid environments and positive retention of sensing elements for minimal risk of foreign object damage. The mechanical packaging is lightweight enough for use in weight and space sensitive aircraft designs and robust enough to withstand the high temperature and vibration associated with rotorcraft powertrain systems. Integral signal conditioning in the controller assembly 200 enables on-line calibration and tuning of the data acquisition in-situ along with communication to integrated vehicle health monitoring systems.

The terminology used herein is for the purpose of describing particular embodiments only and is not intended to be limiting of the invention. While the description of the present invention has been presented for purposes of illustration and description, it is not intended to be exhaustive or limited to the invention in the form disclosed. Many modifications, variations, alterations, substitutions or equivalent arrangements not hereto described will be apparent to those of ordinary skill in the art without departing from the scope and spirit of the invention. Additionally, while the various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A fluid condition monitoring device comprising: a sensing assembly including a sensor and a transducer, the sensor to sense a property of the fluid and the transducer to apply a test signal to the fluid and receive a return signal from the fluid, and the transducer comprising a first electrode and second electrode arranged concentrically, such that the first electrode is arranged radially inward from the second electrode; a control assembly coupled to the sensing assembly, the control assembly including a controller and an input/output interface, the controller interfacing with the transducer to generate fluid condition information in response to the return signal, wherein the controller performs a self-calibration process that includes an automatic gain selection to adjust a gain across a plurality of test signal frequencies; and an interface assembly coupled to the control assembly, the interface assembly including a connection to the input/output interface to transmit the fluid condition information to an external system.

2. The fluid condition monitoring device of claim 1, wherein:
the sensor measures one or both of relative humidity and temperature of the fluid.

3. The fluid condition monitoring device of claim 1, further comprising:
a potting material encompassing the sensor.

4. The fluid condition monitoring device of claim 1, further comprising:
an insulator positioned between the first electrode and the second electrode.

5. The fluid condition monitoring device of claim 1, wherein:
the sensing assembly includes a biasing member to secure the transducer and the sensor in position.

6. The fluid condition monitoring device of claim 1, wherein: the self-calibration process includes automatic test signal selection to select a subset of test frequencies for use in generating the fluid condition information.

7. The fluid condition monitoring device of claim 1, wherein: the sensing assembly includes a first circuit board, the control assembly includes a control circuit board, and further comprising a flexible circuit board interconnecting the first circuit board and the control circuit board.

8. The fluid condition monitoring device of claim 1, wherein:
the control assembly includes a control circuit board mounted in a board support, the board support including at least one shock absorber to absorb force at the control assembly.

9. The fluid condition monitoring device of claim 1, wherein: the fluid condition monitoring device is configured to determine at least one of water content, incorrect fluid addition, lubricant oxidation degradation, additive depletion, and viscosity.

10. The fluid condition monitoring device of claim 1, wherein:
the fluid condition information comprises at least one of dielectric properties, conductivity, and fluid impedance.

11. The fluid condition monitoring device of claim 1, wherein:
the fluid condition monitoring device is positioned in at least one of an in-line flow path, an on-line flow path and an off-line flow path.

12. The fluid condition monitoring device of claim 1, wherein:
the fluid is a lubricant.

13. The fluid condition monitoring device of claim 1, wherein:
the control assembly includes a control circuit board mounted in a board support, the board support being configured to absorb force at the control assembly.

* * * * *